US012708447B2

(12) United States Patent
Glaser et al.

(10) Patent No.: US 12,708,447 B2
(45) Date of Patent: Aug. 18, 2026

(54) SPINOUS PROCESS CLAMP REGISTRATION AND METHODS FOR USING THE SAME

(71) Applicant: WARSAW ORTHOPEDIC, INC., Warsaw, IN (US)

(72) Inventors: Adam David Glaser, Collierville, TN (US); Daniel Paxton Wall, Cordova, TN (US)

(73) Assignee: WARSAW ORTHOPEDIC, INC., Warsaw, IN (US)

(*) Notice: Subject to any disclaimer, the term of this patent is extended or adjusted under 35 U.S.C. 154(b) by 965 days.

(21) Appl. No.: 17/831,907

(22) Filed: Jun. 3, 2022

(65) Prior Publication Data

US 2023/0389991 A1 Dec. 7, 2023

(51) Int. Cl.

| | |
|---|---|
| ***A61B 34/20*** | (2016.01) |
| ***A61B 17/70*** | (2006.01) |
| ***A61B 34/30*** | (2016.01) |
| ***A61B 90/00*** | (2016.01) |
| ***G16H 20/40*** | (2018.01) |
| *A61B 34/10* | (2016.01) |

(52) U.S. Cl.

CPC .......... *A61B 34/20* (2016.02); *A61B 17/7074* (2013.01); *A61B 34/30* (2016.02); *G16H 20/40* (2018.01); *A61B 2034/107* (2016.02); *A61B 2034/2072* (2016.02); *A61B 2090/3916* (2016.02); *A61B 2090/3991* (2016.02)

(58) Field of Classification Search

CPC ... A61B 34/20; A61B 34/30; A61B 2034/107; A61B 2034/2072; A61B 2090/3916; A61B 2090/3991; G16H 20/40

See application file for complete search history.

(56) References Cited

U.S. PATENT DOCUMENTS

| | | | | |
|---|---|---|---|---|
| RE45,509 E * | 5/2015 | Foley | A61B 34/20 600/426 |
| 9,724,165 B2 | 8/2017 | Arata et al. | |
| 10,194,993 B2 | 2/2019 | Roger et al. | |
| 10,335,236 B1 * | 7/2019 | Murphy | A61B 34/30 |
| 2004/0019263 A1 | 1/2004 | Jutras et al. | |
| 2019/0083179 A1 | 3/2019 | Kheradpir et al. | |
| 2020/0405395 A1 | 12/2020 | Gullotti et al. | |
| 2023/0137702 A1 * | 5/2023 | Henderson | A61B 34/20 600/424 |

FOREIGN PATENT DOCUMENTS

WO WO 2021/207471 10/2021

OTHER PUBLICATIONS

International Search Report and Written Opinion for International (PCT) Patent Application No. PCT/IB2023/055413, dated Sep. 7, 2023, 15 pages.

* cited by examiner

*Primary Examiner* — Chao Sheng
(74) *Attorney, Agent, or Firm* — Sheridan Ross PC

(57) ABSTRACT

A method according to at least one embodiment of the present disclosure includes receiving a plurality of images, the plurality of images depicting a navigation probe contacting a plurality of divots on a medical instrument; receiving information about the medical instrument; and determining, based on the plurality of images and the information, a pose of the medical instrument.

20 Claims, 13 Drawing Sheets

100
106A
102
108C
110
116
104A
108A
108B
104B
120
106B
124
115
114

100
102
106B
108C
120
112
110
114
104B
108B
108A
104A
106A
115
116

Receive a plurality of images depicting a navigation probe contacting a plurality of divots on a medical instrument — 804

Register, based on the plurality of images, each divot of the plurality of divots — 808

Receive information about the medical instrument — 812

Determine, based on the received information about the medical instrument and the registration of each divot, a position of the medical instrument — 816

Determine, based on the plurality of images, a position of a moveable component divot relative to at least one divot of the plurality of divots — 820

Determine, based on the position of the moveable component divot and the information about the medical instrument, an angle of the medical instrument — 824

Register the medical instrument to an anatomical element — 828

Update, based on the position and angle of the medical instrument, a surgical plan — 832

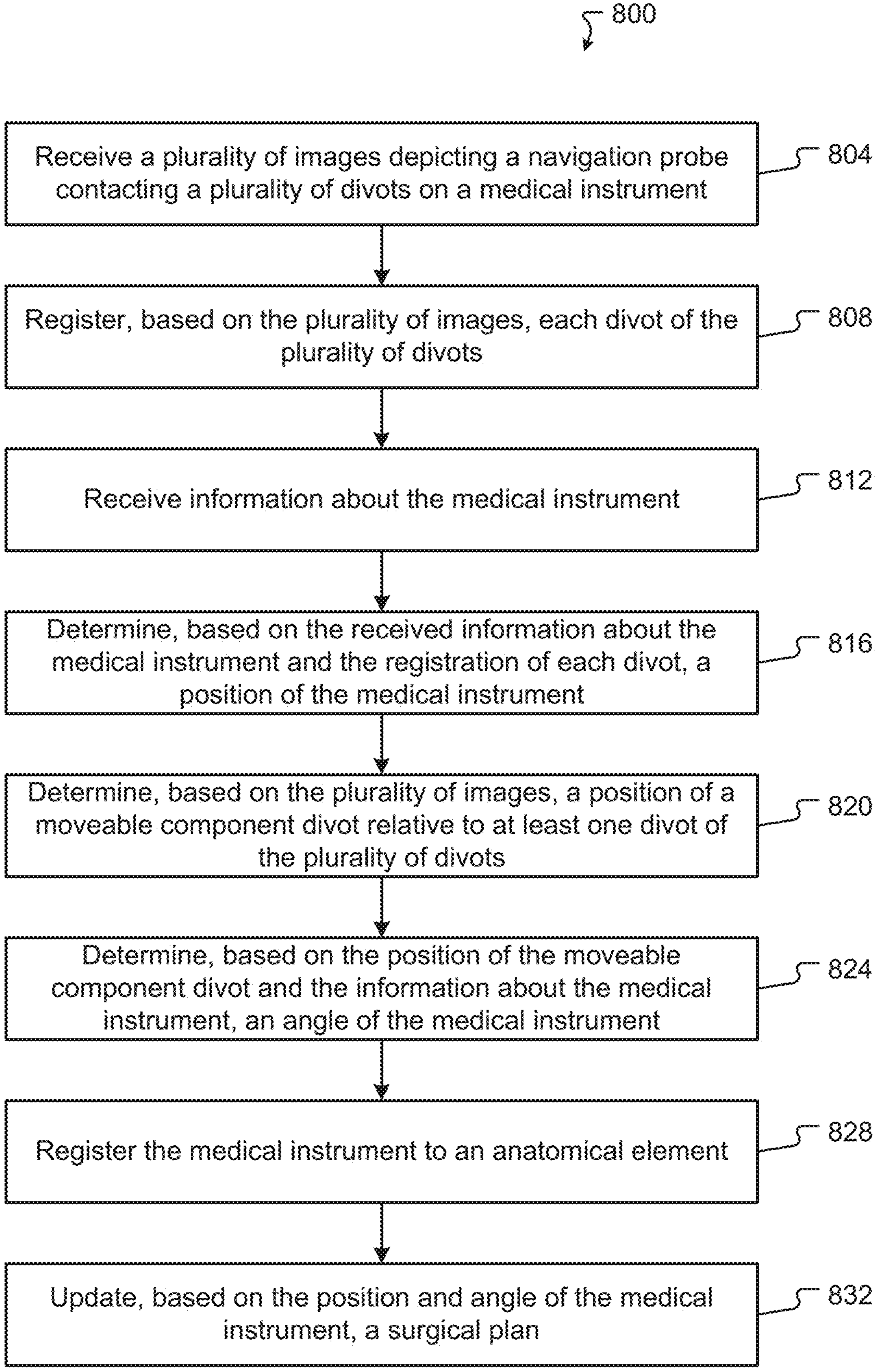

FIG. 8

SPINOUS PROCESS CLAMP REGISTRATION AND METHODS FOR USING THE SAME

BACKGROUND

The present disclosure is generally directed to surgical registration, and relates more particularly to registering a clamp.

Surgical robots may assist a surgeon or other medical provider in carrying out a surgical procedure, or may complete one or more surgical procedures autonomously. Imaging may be used by a medical provider for diagnostic and/or therapeutic purposes. Patient anatomy and tool placement can change over time, particularly following placement of a medical implant in the patient anatomy.

BRIEF SUMMARY

Example aspects of the present disclosure include:

A method according to at least one embodiment of the present disclosure comprises: receiving a plurality of images, the plurality of images depicting a navigation probe contacting a plurality of divots on a medical instrument; receiving information about the medical instrument; and determining, based on the plurality of images and the information, a pose of the medical instrument.

Any of the features herein, further comprising: updating, based on the pose of the medical instrument, a surgical plan.

Any of the features herein, wherein updating the surgical plan further comprises: registering the medical instrument to an anatomical element; and determining, based on the registering, a new trajectory for a surgical implant.

Any of the features herein, wherein the surgical implant includes a pedicle screw.

Any of the features herein, wherein the medical instrument comprises a bone mounting device, and wherein the information about the medical instrument comprises information about a pre-configured orientation of the plurality of divots.

Any of the features herein, wherein determining the pose of the medical instrument further comprises: determining a pose of a plurality of tracking markers on the navigation probe when the navigation probe contacts each divot of the plurality of divots; and determining, based on the pre-configured orientation and the determined pose of the tracking markers, a position of the medical instrument.

A system according to at least one embodiment of the present disclosure comprises: a processor; and a memory storing data thereon that, when processed by the processor, cause the processor to: receive a plurality of images depicting a navigation probe contacting a plurality of divots on a surgical device; receive information about the surgical device; and determine, based on the plurality of images and the information about the surgical device, a pose of the surgical device.

Any of the features herein, wherein the data further cause the processor to: update, based on the pose of the surgical device, a surgical plan.

Any of the features herein, wherein updating the surgical plan further comprises: registering the surgical device to an anatomical element; and updating, based on the registering, a trajectory of a surgical implant.

Any of the features herein, wherein the surgical device comprises: an upper body; a clamp connected to the upper body and that attaches the surgical device to an anatomical element; and a tightening mechanism that secures the clamp to the anatomical element.

Any of the features herein, wherein the plurality of divots include a first divot, a second divot, and a third divot each disposed on the upper body, and a fourth divot disposed on the tightening mechanism.

Any of the features herein, wherein the data further cause the processor to: receive at least one image depicting the navigation probe contacting the fourth divot; determine, based on the at least one image and the information about the surgical device, a position of the fourth divot relative to at least one of the first divot, the second divot, or the third divot; and determine, based on the position, an angle of the surgical device relative to the anatomical element.

Any of the features herein, wherein each divot of the plurality of divots includes a first geometric shape, and wherein the first geometric shape is one of a circle, a triangle, a square, a rectangle, a pentagon, a hexagon, a heptagon, an octagon, a nonagon, a decagon, an ellipse, a trapezoid, a parallelogram, a rhombus, a cross or a plus, a pentagram, a hexagram, an octagram, or a crescent.

An apparatus according to at least one embodiment of the present disclosure comprises: an imaging device; a bone mount device configured to attach to an anatomical element and including a plurality of divots; a processor; and a memory storing data thereon that, when processed by the processor, cause the processor to: receive a plurality of images from the imaging device depicting a plurality of navigation markers disposed on a navigation probe contacting the plurality of divots; receive information about an orientation of the plurality of divots; and determine, based on the plurality of images and the information about the orientation of the plurality of divots, a pose of the bone mount device.

Any of the features herein, wherein the data further cause the processor to: update, based on the pose of the bone mount device, a surgical plan.

Any of the features herein, wherein updating the surgical plan further comprises: registering the bone mount device to the anatomical element; and updating, based on the registering, a trajectory for a surgical implant.

Any of the features herein, wherein the bone mount device further comprises: an upper body; a clamp connected to the upper body; and a moveable component that attaches the clamp to the anatomical element.

Any of the features herein, wherein the plurality of divots includes a first divot, a second divot, and a third divot, wherein the moveable component includes a fourth divot.

Any of the features herein, wherein the navigation probe is substantially perpendicular to a surface of the bone mount device when contacting at least one of the first divot, the second divot, the third divot, or the fourth divot.

Any of the features herein, wherein the bone mount device is attached to a spinous process of a vertebra, and wherein the apparatus further comprises: a connector coupled to the bone mount device at a first end and coupled to a robotic arm at a second end.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present disclosure will become apparent to those skilled in the art upon consideration of the embodiment descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 8 shows a flowchart in accordance with embodiments of the present disclosure.

DETAILED DESCRIPTION

Figure 1B:
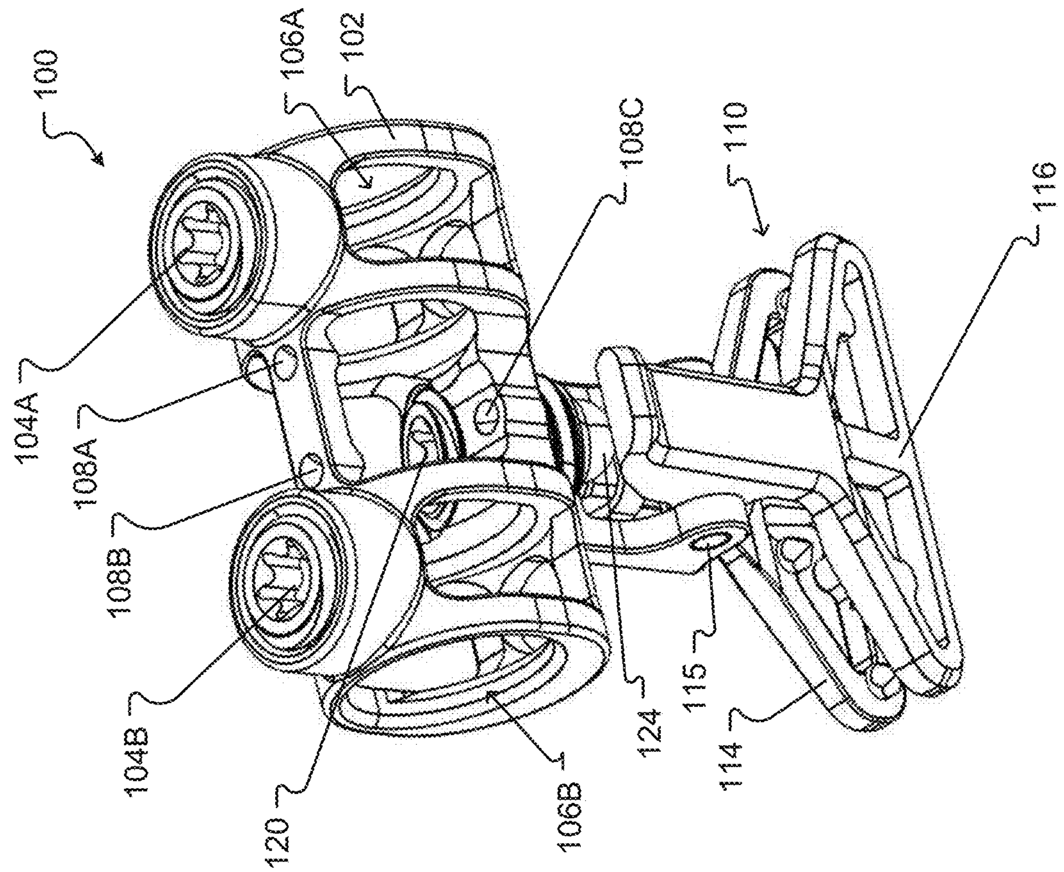
FIG. 1B shows an alternative perspective view of the bone mount device in accordance with embodiments of the present disclosure.
Figure 1A:
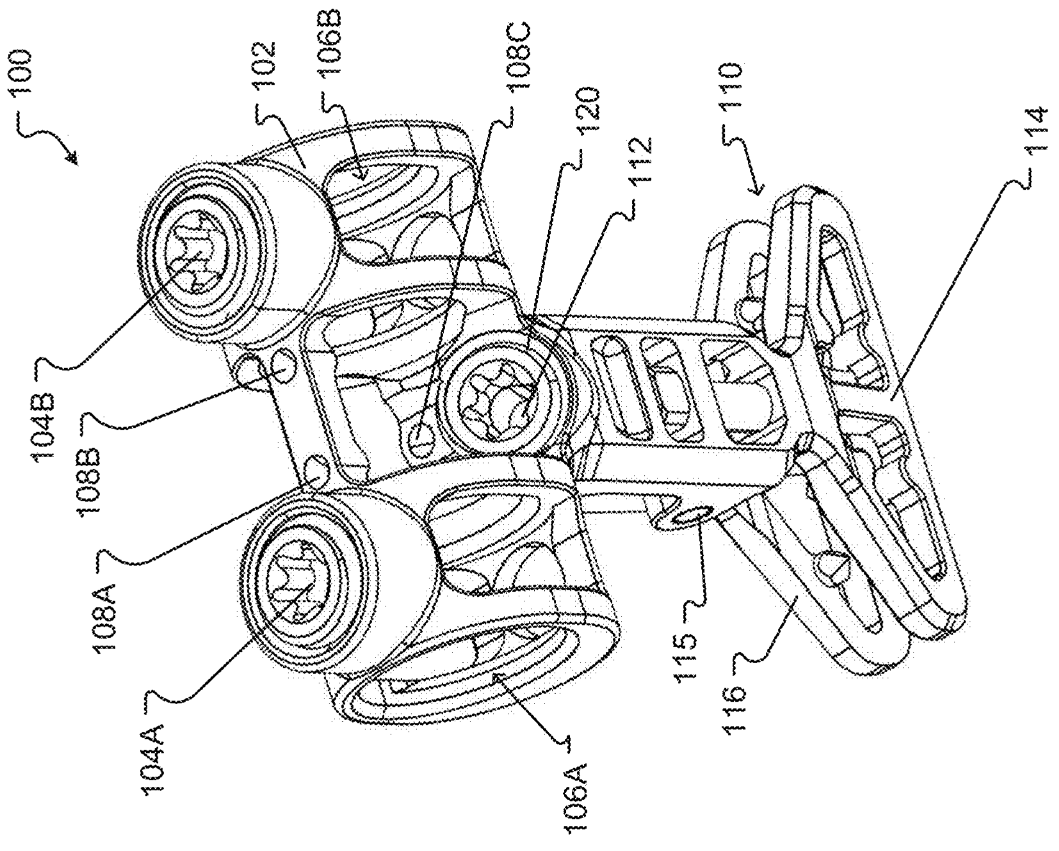
FIG. 1A shows a perspective view of a bone mount device in accordance with embodiments of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

When planning for screw insertion for a surgery or surgical procedure, there is no way to represent bone mount hardware on a screen to a surgeon. The surgery or surgical procedure may include screws or with other surgical instruments that may interfere one or more surgical clamps (e.g., spinous process clamps) or other bone mount devices. Surgeons could benefit from having a way to represent clamps and other hardware in three-dimensional (3D) space after mounting the hardware to a bone, beneficially enabling more accurate placement of screws in relation to anatomy and bone mount devices. For instance, after placing a spinous process clamp, it would be beneficial to know where the clamp is in 3D space to avoid collisions with the clamp (such as when inserting pedicle screw). By providing a 3D representation of the clamp (e.g., rendered to screen or other user display), the surgeon may be able to plan trajectories of other medical implants (e.g., surgical screws) to avoid collisions between the medial implants and the clamp.

In at least one embodiment of the present disclosure, a bone mount device may include three or more divots that can be used to register the bone mount device. The three or more divots can each be contacted using a navigation probe, with captured images of the navigation probe used to generate a location of the bone mount device that can be used by a navigation system. If the bone mount device includes a moveable component, a fourth divot can be added that can be used to generate the location of the movable component in relation to the original three divots. The software or processor may calculate the position of the moving component based on the original position of the three divots and the measured position of the movable component relative to the three divots. Based on the captured images, systems and methods of the present disclosure may be used to register the divot points on the clamp to a common coordinate system. For example, the three divots may create three points for providing a coordinate system, with the coordinate system used to place a 3D representation of the clamp into other 3D scans, such that a navigation system knows where the clamp is relative to one or more anatomical elements.

In at least one embodiment of the present disclosure, a system may provide a user (e.g., a surgeon) with an ability to select a "define clamp" or similar feature (e.g., by selecting a prompt on a user interface such as a touch screen). Upon selection, the system may ask the user to select the three or more divots on the clamp. As the user selects each divot, an imaging device could capture an image of the navigation probe. Further, the user may provide an identification number or part number associated with the clamp. The system may then determine, based on the identification number and the series of images, a pose of the clamp relative to one or more anatomical elements.

As previously noted, if the clamp includes a moveable component (e.g., a set screw that can be adjusted to change how tightly the clamp grips the vertebra or other anatomical element), the user may be prompted to select a fourth divot to define the location of the movable component. The system may then use the pose of the navigation probe to determine a position of the fourth divot relative to the other three divots. Based on the position of the fourth divot relative to, for example, the third divot (or any other divot), the system may determine an angle of the clamp relative to the anatomical element and/or other portions of the clamp.

In at least one embodiment of the present disclosure, a post may be used to determine the pose of the clamp. The post may include a navigation tracker, and may engage with the bone mount device. The user may insert the custom post with the tracker into the bone mount device, and the custom post may, when inserted, move to a specific orientation in 3D space. Once the custom post is connected with the bone mount device, the user may provide the system with an identification number of the custom post, or otherwise instruct the system on which bone mount device is connected to the custom post. Additionally, the bone mount device in such embodiments may include the fourth divot that can be used to control screw position and clamp angle.

Embodiments of the present disclosure provide technical solutions to one or more of the problems of (1) collisions between a surgical implant and one or more other surgical devices near an implant location, and (2) bone mount device pose (e.g., position and orientation) uncertainty.

Turning first to FIGS. 1A-2B, various views of a bone mount device 100 are depicted in accordance with at least one embodiment of the present disclosure. The bone mount device 100 may be capable of connecting or attaching to, or otherwise mechanically coupling with, one or more anatomical elements (e.g., vertebrae). The bone mount device 100 may also connect to one or more other surgical components, tools, or other instruments (e.g., a robotic arm) to rigidly connect the surgical components to the anatomical elements.

Figure 2A:
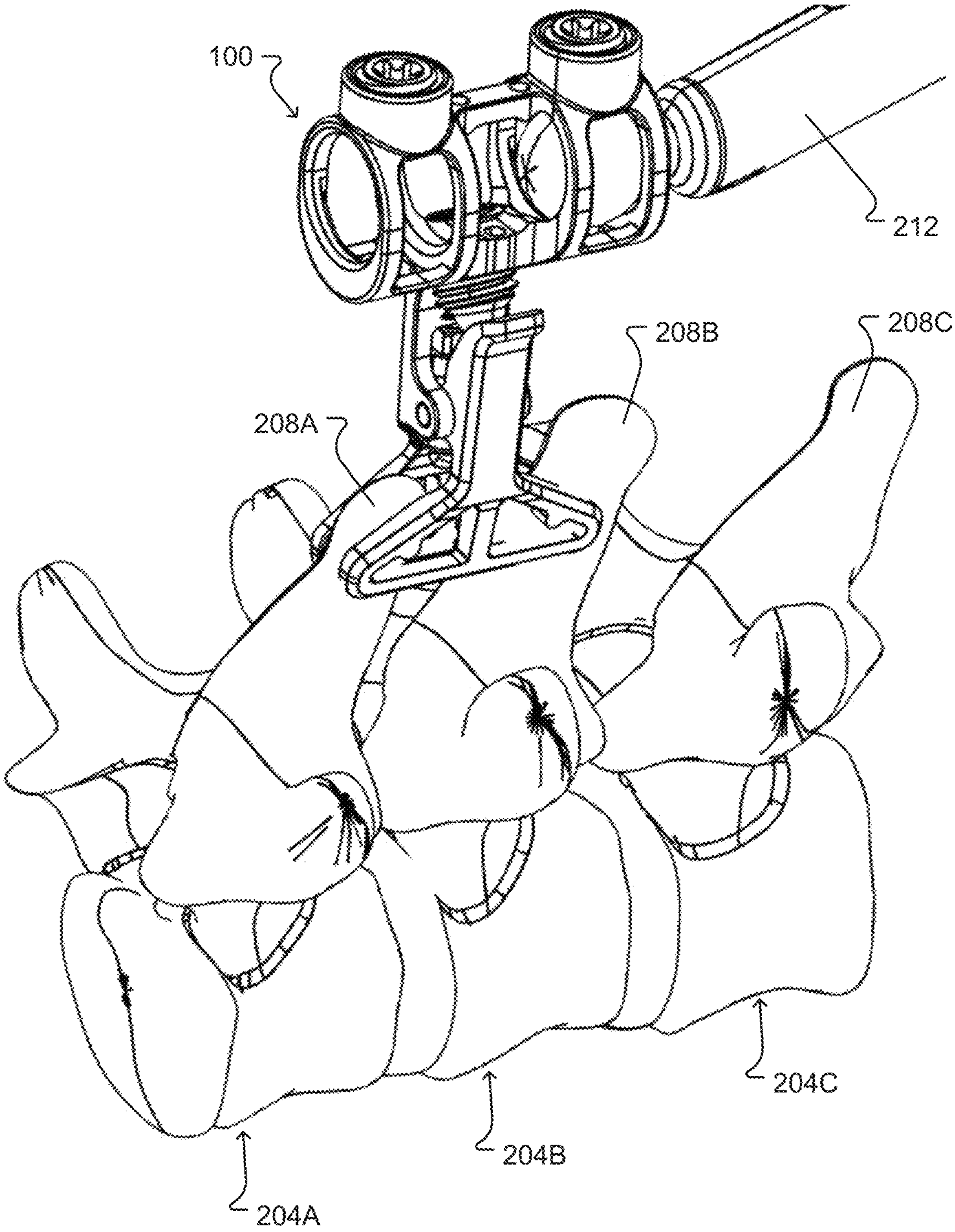
FIG. 2A shows a perspective view of the bone mount device connected to an anatomical element in accordance with embodiments of the present disclosure.

The bone mount device 100 may include an upper body 102. The upper body 102 may provide locations for the one or more surgical components to connect to the bone mount device 100. The upper body 102 may include one or more cavities, ports, slots, or other connection mechanisms that enable the surgical components to be attached to the bone mount device 100. For example, the upper body 102 may include a first port 106A and a second port 106B into which connectors may be inserted. The first port 106A may include a first screw 104A and the second port 106B may include a second screw 104B, with each screw 104A, 104B capable of, for example, being tightened or loosened to secure the surgical component in the first port 106A and the second port 106B, respectively. As shown in FIG. 2A, a connector 212 may be inserted into the first port 106A, and the first screw 104A may be adjusted to secure the connector 212 in the first port 106A. The connector 212 may in turn be connected to a robotic arm, such that, by connecting the connector 212 to the bone mount device 100, the robotic arm can be connected to the anatomical element to which the bone mount device 100 is connected, such as to a first vertebra 204A. The connection between the robotic arm and the anatomical element may beneficially enable a navigation system to determine the pose of the robotic arm relative to the anatomical element to, for example, navigate the robotic arm relative to the anatomical element.

The upper body 102 may also include a plurality of divots 108. The plurality of divots 108 may include a first divot 108A, a second divot 108B, and a third divot 108C disposed in a preconfigured orientation on one or more surfaces of the upper body 102. The plurality of divots 108 may be or comprise indentations or other concave structures on the surfaces of the upper body 102. In some embodiments, one or more divots of the plurality of divots 108 may be disposed on other locations of the bone mount device 100 or, in other words, may not be disposed on the upper body 102. It is to be understood that, while three divots are depicted, the number of divots is in no way limited, and additional or alternative numbers of divots may be present or used.

In some embodiments, the plurality of divots 108 may be reflective, radiopaque, or may otherwise be detectable in the captured images. In such embodiments, the plurality of divots 108 may appear in the captured images, and image processing may be used to identify or label the plurality of divots 108. The labeling may then enable the pose of the bone mount device 100 to be determined based at least in part on the identified locations. Additionally or alternatively, the plurality of divots 108 may be viewed by a navigation system (e.g., images are not captured), and the visible landmarks created by the plurality of divots 108 may be registered to other known markers or locations known to the navigation system (e.g., to a navigation marker on a robotic arm) to enable the navigation system to determine the position of the bone mount device 100.

The plurality of divots 108 may include one or more geometric shapes. The geometric shapes may be engraved into one or more divots of the plurality of divots 108, or may alternatively be the overall shape of the divot. The geometric shapes may enable coupling between the divot and a tip of a navigation probe when the navigation probe is used to determine a pose of the bone mount device 100. For example, the tip of the navigation probe may have a spherical tip, and the divots may each include a concave spherical shape, such that the navigation probe tip fits into the divot. In another example, the tip of the navigation probe may have a triangle shape, and the divots may each have a triangular indent, such that the tip of the navigation probe slots into the triangular indent of each divot to align the tip of the navigation probe with the divot. In this example, the triangular indent may ensure that the tip (and by extension the navigation probe) is substantially perpendicular to the surface of the bone mount device 100 when the tip is coupled with the divot. In other embodiments, the tip of the navigation probe may be able to couple with the divot at an angle, such that the navigation probe tip enters the divot at an angle.

In some embodiments, each divot may have a different geometric shape than any of the other divots. For instance, the first divot 108A may have a first geometric shape, the second divot 108B may have a second geometric shape, and the third divot 108C may have a third geometric shape. In other embodiments, any one divot may share a common geometric shape with one or more other divots. For example, both the first divot 108A and the second divot 108B may both have a first geometric shape, while the third divot 108C may have a second geometric shape. The type of geometric shape of the divot is in no way limited, and examples of geometric shapes include a circle, a triangle, a square, a rectangle, a pentagon, a hexagon, a heptagon, an octagon, a nonagon, a decagon, an ellipse, a trapezoid, a parallelogram, a rhombus, a cross or plus, a pentagram, a hexagram, an octagram, a crescent, and the like.

The bone mount device 100 may include a clamp 110. The clamp 110 may include a first jaw 114 and a second jaw 116. The first jaw 114 and the second jaw 116 may be or comprise components that enable connection of the bone mount device 100 to an anatomical element such as a first vertebra 204A. As shown in FIG. 2A, the bone mount device 100 may be connected to one or more vertebrae 204A-204C, such as the spinous process 208A and the spinous process 208B of the first vertebra 204A and a second vertebra 204B, respectively. In other embodiments, the clamp 110 may be configured to attach the bone mount device 100 to another portion of a vertebra, such as to the transverse process of a vertebra.

The clamp 110 may include a set screw 120. The set screw 120 may be or comprise a tensioning or tightening mechanism to secure the clamp 110 (and by extension the bone mount device 100) to an anatomical element. The set screw 120 may be or comprise a screw or other moveable component capable of adjusting the position of the first jaw 114 and/or the second jaw 116 to connect the bone mount device 100 to the anatomical element. The set screw 120 may be threaded and inserted through the upper body 102 to contact the second jaw 116 at a contact point 124. To attach the bone mount device 100 to the anatomical element, the bone mount device 100 may be positioned such that the first jaw 114 is disposed on a first side of the anatomical element and the second jaw 116 is positioned on a second side of the anatomical element, such as a first side and a second side of a spinous process of a vertebra, respectively. The set screw

120 may then be inserted (e.g., screwed into) into the upper body 102 with the body of the set screw 120 contacting the second jaw 116 at the contact point 124. As the set screw 120 is tightened (e.g., by twisting the set screw 120 using a screwdriver or other tool), the set screw 120 may apply a force to an upper portion of the second jaw 116. The second jaw 116 may then pivot about a connection point 115 toward the first jaw 114. As the set screw 120 is tightened, the force on the upper part of the second jaw 116 may increase until the bone mount device 100 is secured to the anatomical element.

The set screw 120 may include a fourth divot 112. The fourth divot 112 may be an adjustor or adjustment divot disposed in a hollow interior of the set screw 120 or other moveable component, and may be accessible by the tip of the navigation probe. As described in further detail below, the fourth divot 112 may be used to determine an angle of the bone mount device 100 relative to the anatomical element, which may beneficially enable a navigation system to avoid contacting the bone mount device 100 during a surgery or surgical procedure.

The bone mount device 100 may include a part number, identification number, or other form of identifier. The part number may reflect information about the bone mount device 100, such as the dimensions (e.g., length, width, depth, etc.) of the bone mount device 100, the geometry of the plurality of divots 108 (e.g., triangular divots), information about the orientation of the plurality of divots 108 (e.g., how far away first divot 108A is from second divot 108B in 3D space), combinations thereof, and the like. In one embodiment, the part number may enable a navigation system to determine a set of coordinates for the bone mount device 100. For example, the part number may be a unique identifier for the bone mount device 100, such that by knowing the part number, the navigation system can determine the coordinates of the plurality of divots 108 and/or a 3D model of the bone mount device 100. In such examples, the part number may be provided by a user (e.g., a surgeon) and the navigation system may use the number to identify the corresponding bone mount device 100 (and information related thereto such as a volume occupied by the bone mount device 100) in, for example, a database or other data storage unit. The navigation system may then use the information to determine a pose of the bone mount device 100 when the bone mount device 100 is mounted to an anatomical element.

Figure 2B:
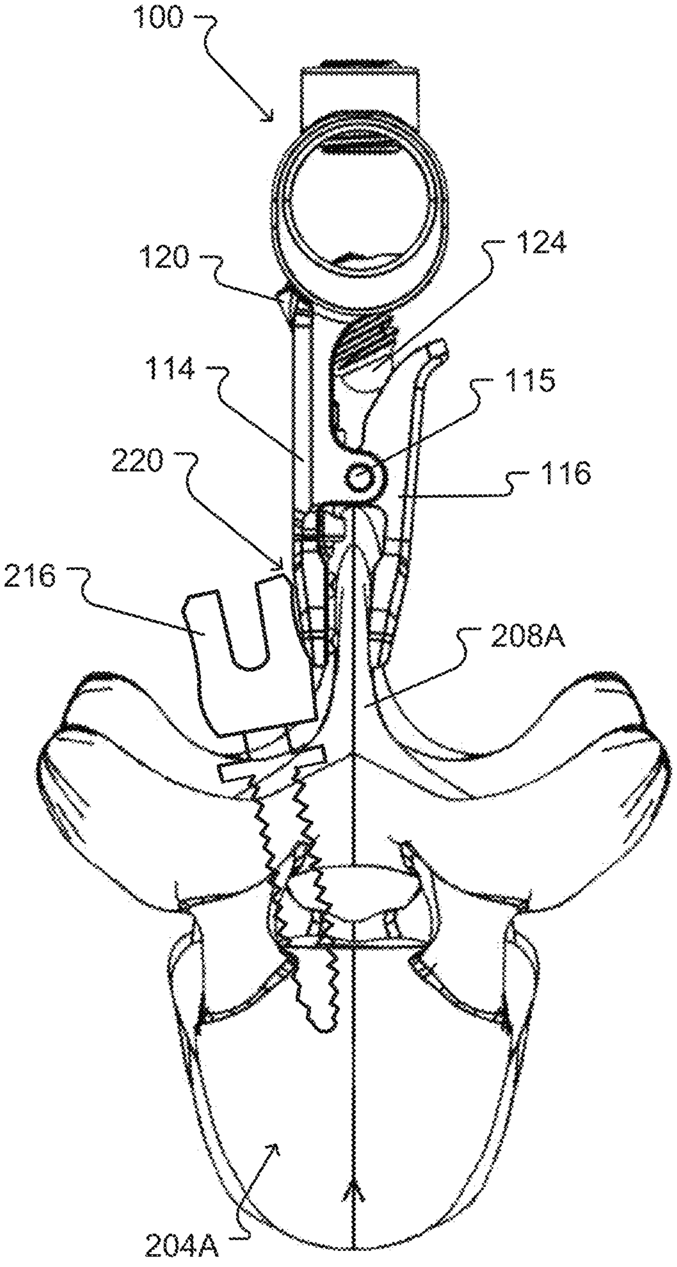
FIG. 2B shows a plan view of the bone mount device connected to the anatomical element in accordance with embodiments of the present disclosure.

When the bone mount device 100 is used in a surgery or surgical procedure, differences in the pose of the bone mount device 100 could impact how a surgical implant is implanted into an anatomical element. As shown in FIG. 2B, for example, a screw 216 may be inserted into a first vertebra 204A, but a potential risk in inserting the screw 216 without knowing a pose of the bone mount device 100 is that a collision 220 may occur between the screw 216 and the bone mount device 100 as the screw 216 is moved and screwed into place, which may result in surgeon dissatisfaction, reduced efficiency of the surgical procedure, and/or patient harm. To address such issues, the pose of the bone mount device 100 may be determined and the trajectory of the screw 216 may be adjusted, as discussed in detail herein.

Figure 3A:
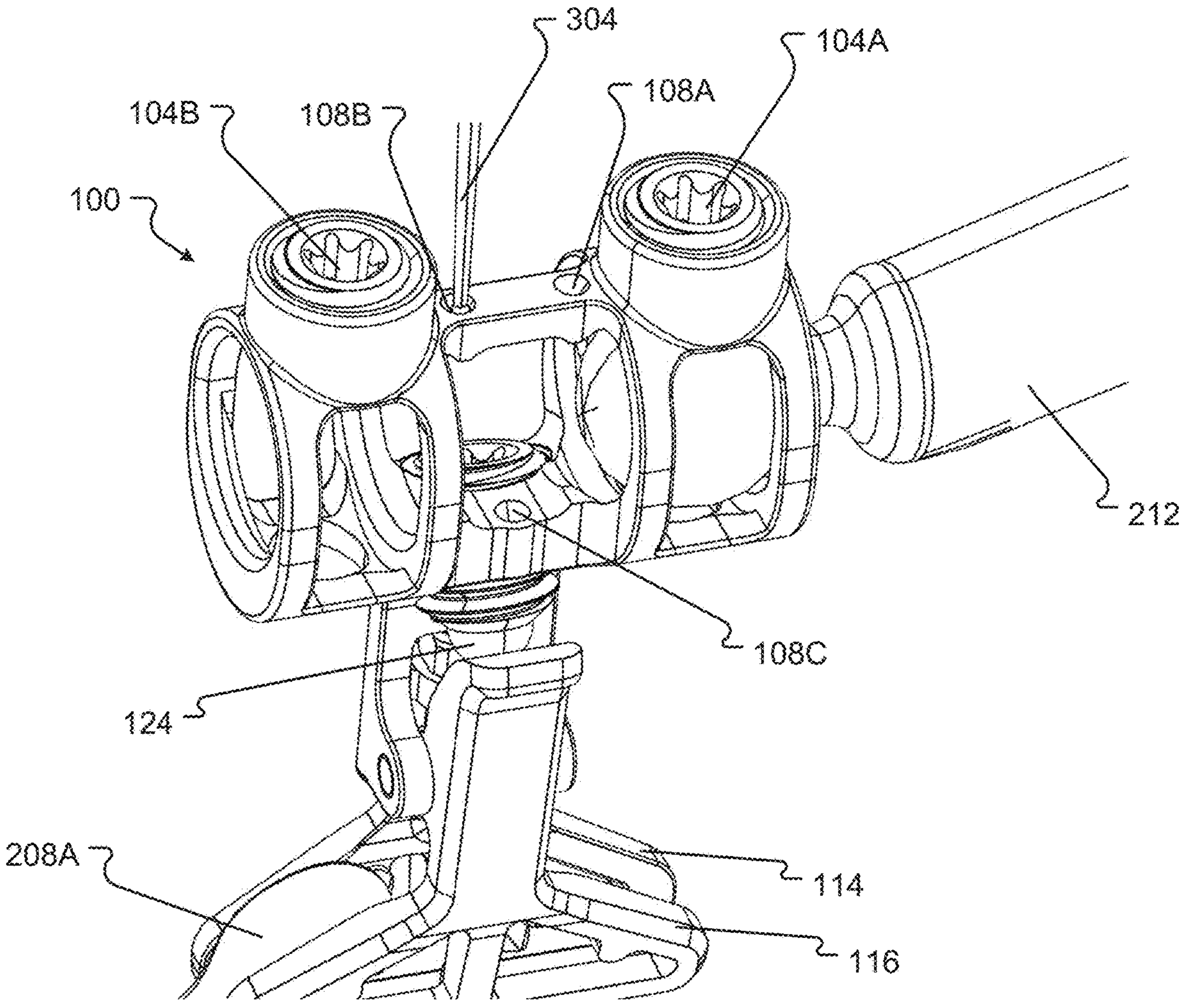
FIG. 3A shows a perspective view of the bone mount device with a first divot contacted by a navigation probe in accordance with embodiments of the present disclosure.
Figure 3B:
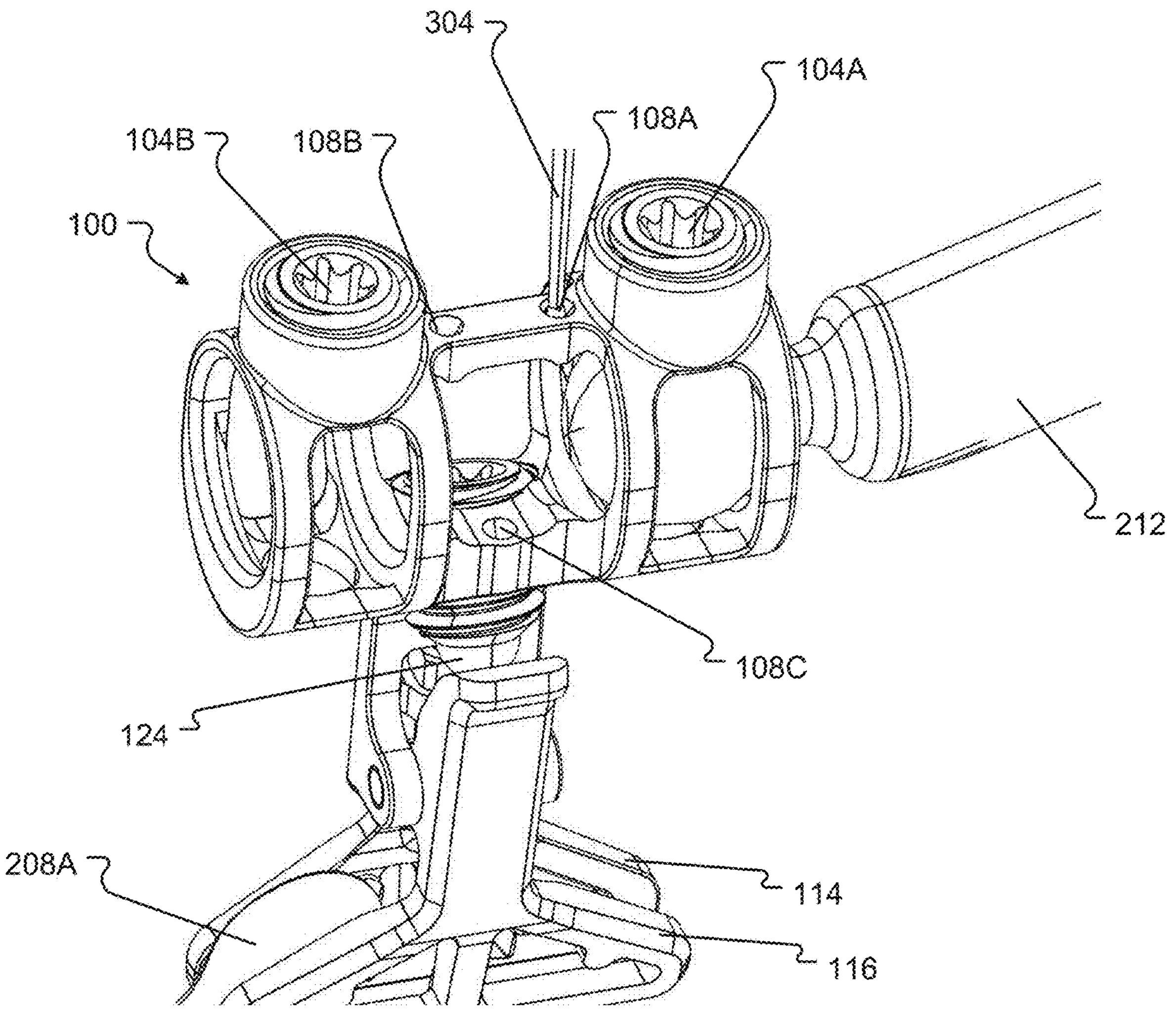
FIG. 3B shows a perspective view of the bone mount device with a second divot contacted by the navigation probe in accordance with embodiments of the present disclosure.
Figure 3C:
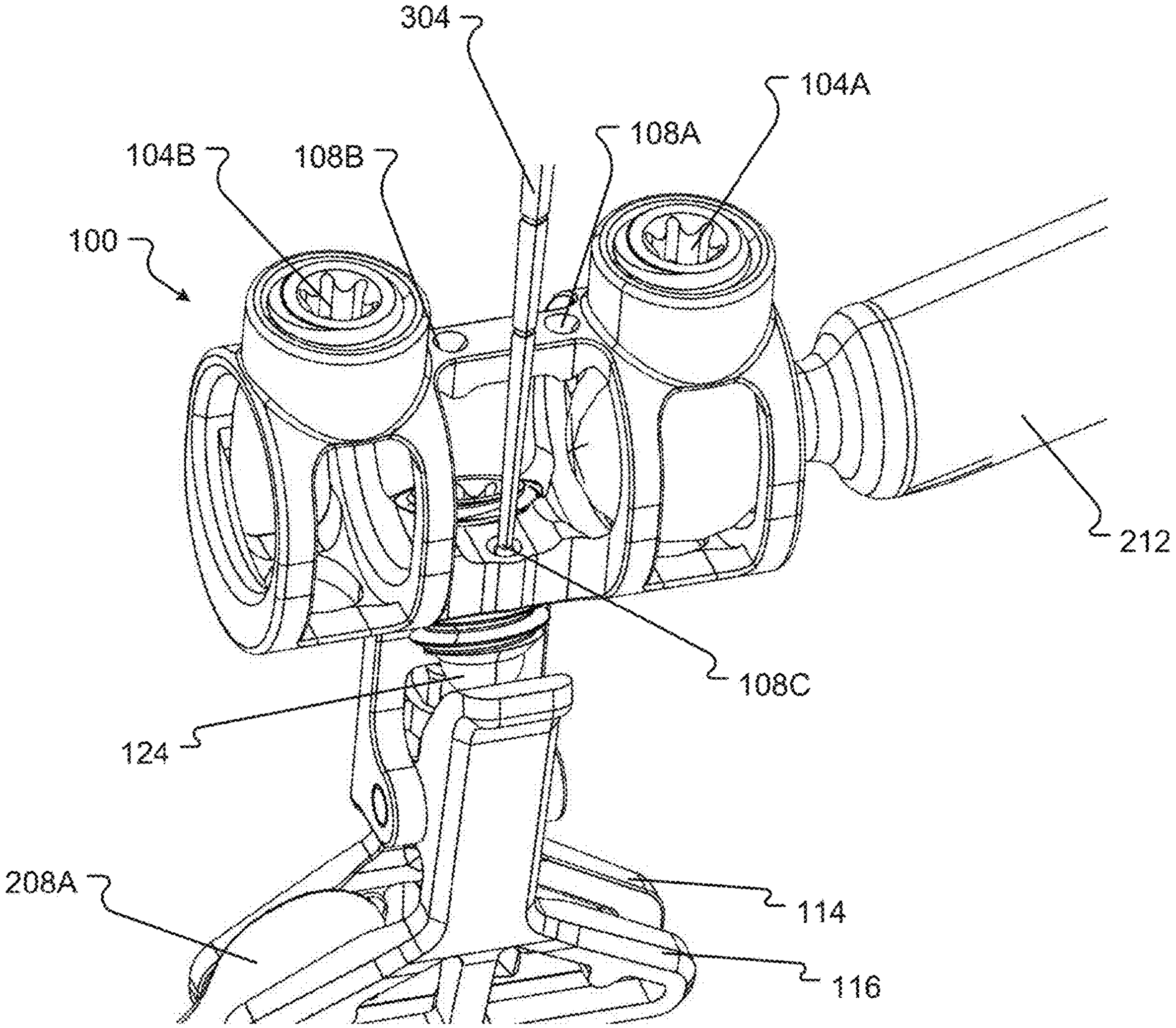
FIG. 3C shows a perspective view of the bone mount device with a third divot contacted by the navigation probe in accordance with embodiments of the present disclosure.

Turning to FIGS. 3A-3C, aspects of the bone mount device 100 connected to anatomical element are shown in accordance with at least one embodiment of the present disclosure. The bone mount device 100 may be connected to a spinous process 208A of a vertebra 204A, with the connector 212 disposed in the first port 106A of the upper body 102. In some embodiments, the bone mount device 100 may be disposed on the spinous process 208A during the course of a surgery or surgical procedure. For example, the bone mount device 100 may be used to physically couple the connector 212 to the anatomical element, with the connector 212 further connected to a robotic arm. This coupling may couple the robotic arm to the anatomical element, allowing for registration between the robotic arm and the anatomical element and allowing a navigation system to maneuver the robotic arm relative to the anatomical element.

Figure 5:
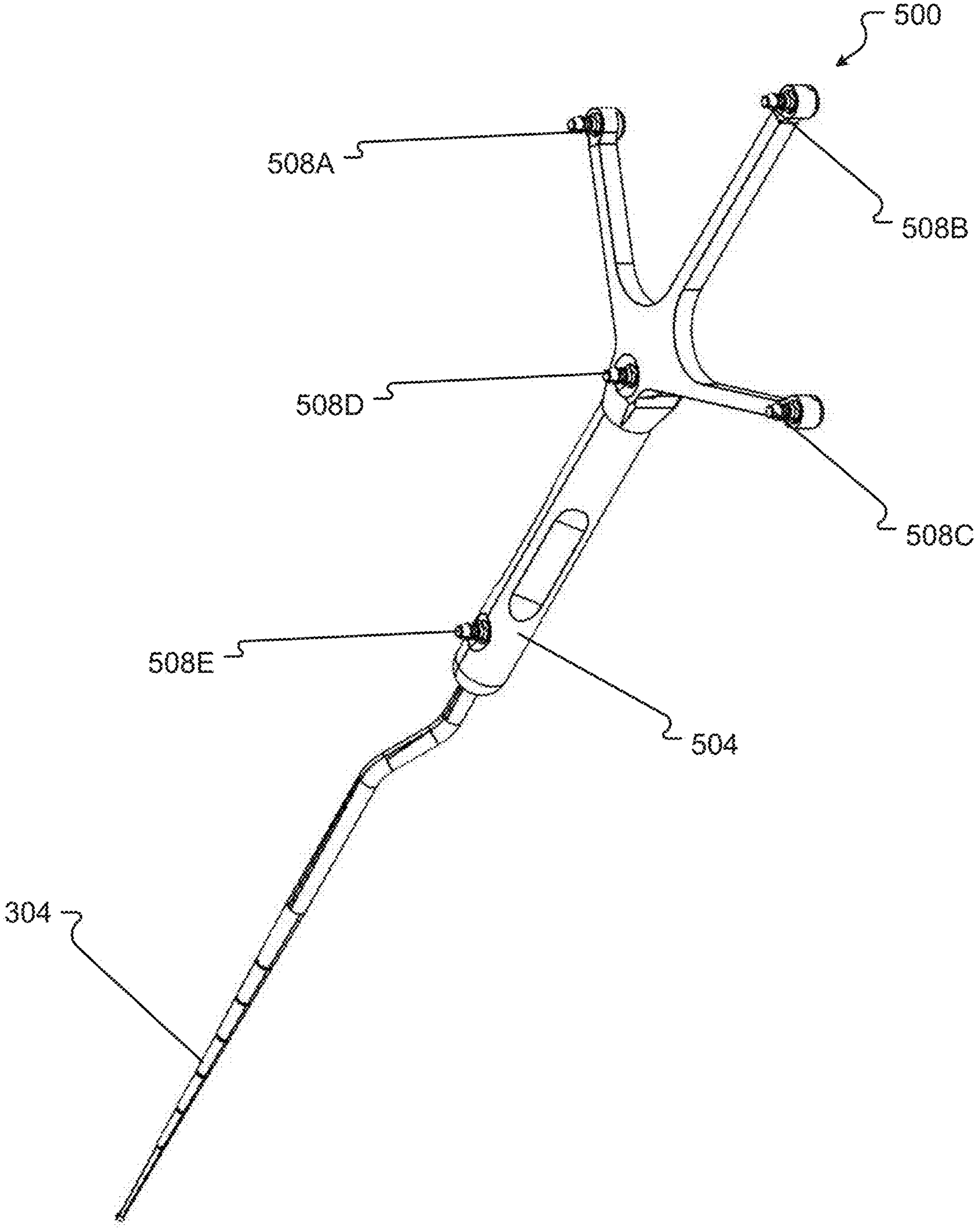
FIG. 5 shows a perspective view of the navigation probe in accordance with embodiments of the present disclosure.

To determine the pose (e.g., the position and orientation, the position and angle, etc.) of the bone mount device 100, a user (e.g., a surgeon) may use a navigation probe tip 304 of a navigation probe 500 to contact each divot of the plurality of divots 108. The navigation probe tip 304 may be part of the navigation probe 500 shown in FIG. 5. The navigation probe 500 may include a body 504 to which one or more tracking markers 508A-508E are attached. The tracking markers 508A-508E may comprise radiopaque elements that enable the navigation system to identify the tracking markers 508A-508E in one or more images (e.g., fluoroscopic images). In some embodiments, the tracking markers 508A-508E may be active (e.g., Light Emitting Diodes (LEDs)) markers or passive markers. The tracking markers 508A-508E may be disposed in a pre-configured orientation on the body 504 based on, for example, a part number or identification number associated with the navigation probe 500. In other words, a navigation system, processor, or other system may be able to determine, based on a received set of images, the pose of the navigation probe 500 based on identified locations of the tracking markers 508A-508E. In some embodiments, the navigation system, processor, or other system may use the identified pose of the navigation probe 500 to facilitate registration the navigation probe 500 and, by extension, the plurality of divots 108 to a common coordinate system shared by other surgical instruments (e.g., a robotic arm) used in a surgery or surgical procedure.

As illustrated in FIGS. 3A-3C, to enable registration of the plurality of divots 108, the navigation probe tip 304 may be inserted into, slotted into, or used to contact the first divot 108A, the second divot 108B, and the third divot 108C. For instance, FIG. 3A shows the navigation probe tip 304 contacting the second divot 108B, FIG. 3B shows the navigation probe tip 304 contacting the first divot 108A, and FIG. 3C shows the navigation probe tip 304 contacting the third divot 108C. As the navigation probe tip 304 contacts each divot, an imaging device (not shown) may capture one or more images of the navigation probe 500 relative to the bone mount device 100. Based on the images, the position of each divot of the plurality of divots 108 and the pose of the bone mount device 100 may be determined, as discussed in further detail below.

Figure 4A:
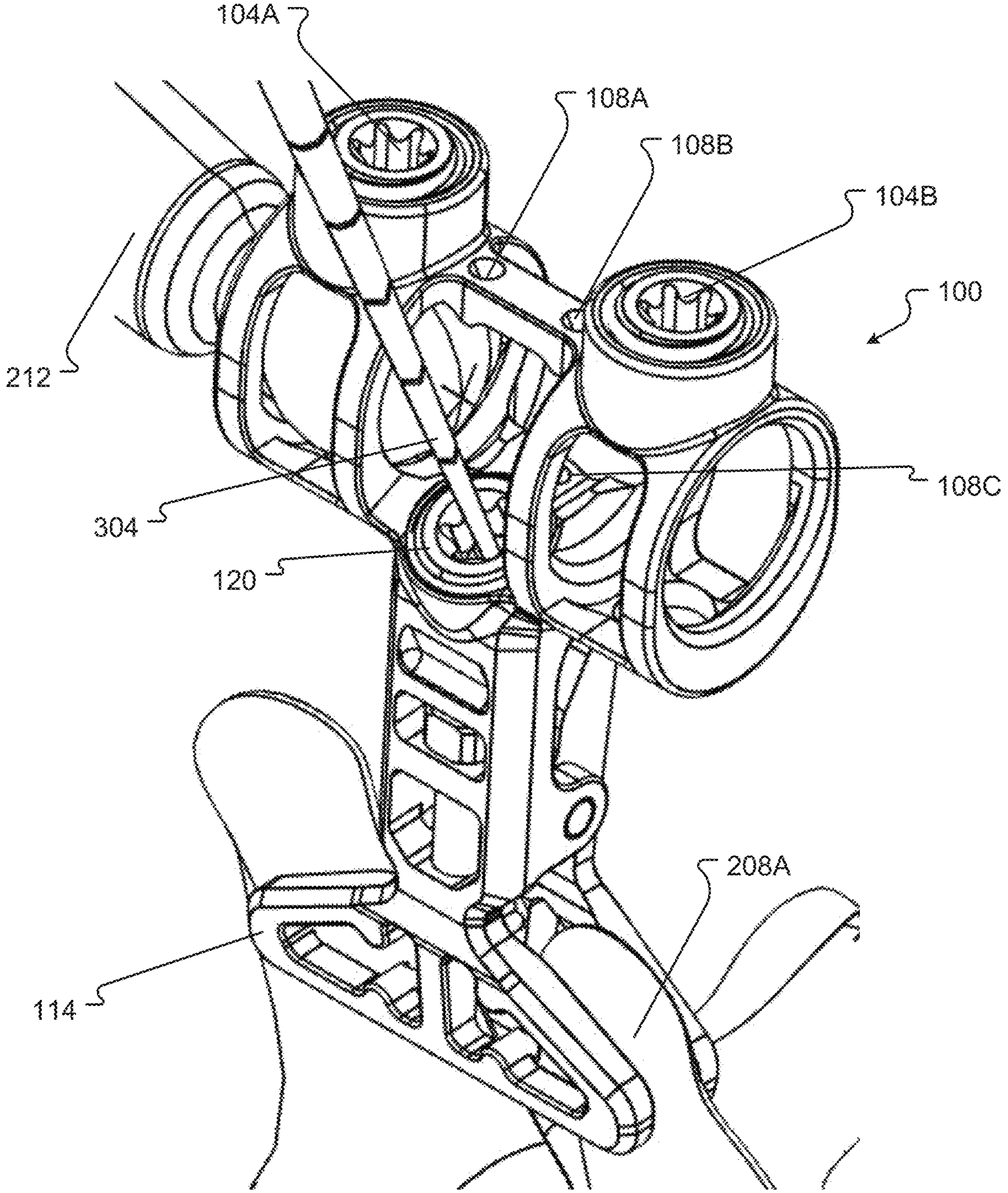
FIG. 4A shows a perspective view of the bone mount device with a fourth divot contacted by the navigation probe in accordance with embodiments of the present disclosure.

Further, the navigation probe tip 304 may be inserted into the fourth divot 112 of a moveable component such as the set screw 120 to enable determination of an angle of the clamp 110 or the bone mount device 100 relative to the anatomical element to which the bone mount device 100 is attached. As shown in FIG. 4A, the fourth divot 112 may be disposed on an interior of the set screw 120, and the navigation probe tip 304 may be inserted into the set screw 120 to contact the fourth divot 112. In some embodiments, the fourth divot 112 may be contacted after the first divot 108A, the second divot 108B, and the third divot 108C have been contacted and the pose of the bone mount device 100 has been determined. In other words, the angle of the bone mount device 100 may be determined after the pose of the bone mount device 100 has been determined.

Figure 4C:
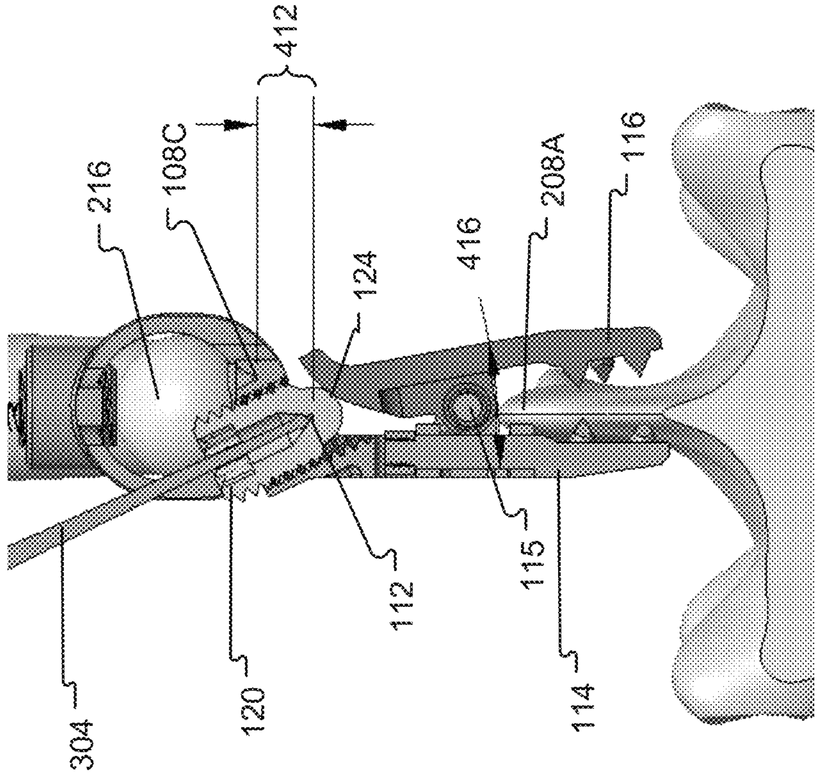
FIG. 4C shows a plan cross-section of the bone mount device with the fourth divot contacted by the navigation probe in a second orientation in accordance with embodiments of the present disclosure.
Figure 4B:
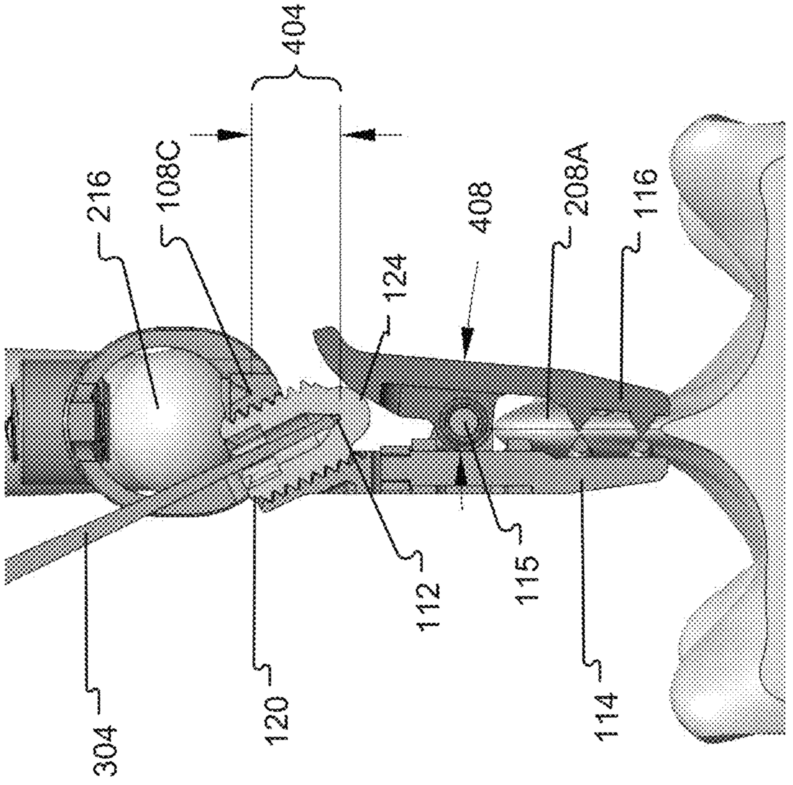
FIG. 4B shows a plan cross-section of the bone mount device with the fourth divot contacted by the navigation probe in a first orientation in accordance with embodiments of the present disclosure.

One or more images of the navigation probe 500 may be captured once the navigation probe tip 304 is inserted into the set screw 120 to contact the fourth divot 112. Based on the determined pose of the navigation probe 500, a processor or other component may determine a position of the fourth divot 112 relative to the third divot 108C or, alternatively, relative to any other divot of the plurality of divots 108. The relative distance between the fourth divot 112 and the third divot 108C may be used to determine an angle of the bone mount device 100. For example, as the set screw 120 moves further down through the upper body 102 to rotate the second jaw 116 about the connection point 115, the further away from the third divot 108C the fourth divot 112 moves. As shown in FIGS. 4B-4C, when the fourth divot 112 is a first distance 404 from the third divot 108C in a first direction such as a height direction, the clamp 110 may be at a first angle 408, and when the fourth divot 112 is a second distance 412 from the third divot 108C, the clamp 110 may be at a second angle 416. For example, when the fourth divot 112 is 9.183 millimeters (mm) from the third divot 108C in a height direction, the clamp 110 may have a corresponding angle of 5 degrees)(5°, and when the fourth divot 112 is 5.836 mm from the third divot 108C in the height direction, the clamp 110 may have an angle of negative 10°. The determination of the angle may beneficially enable the navigation system to update a trajectory of a surgical implant (e.g., a screw 216) based on the determined angle. For example, the navigation system may determine that the trajectory of the screw 216 does not need to be changed when the clamp 110 has an angle of 5° (e.g., the bone mount device 100 will not interfere with the planned insertion of the set screw 120), but may determine that the screw 216 trajectory should be updated when the clamp 110 has an angle of negative 10° (e.g., at the planned trajectory, the angle of the bone mount device 100 is such that the screw 216 would collide with the bone mount device 100).

Figure 6A:
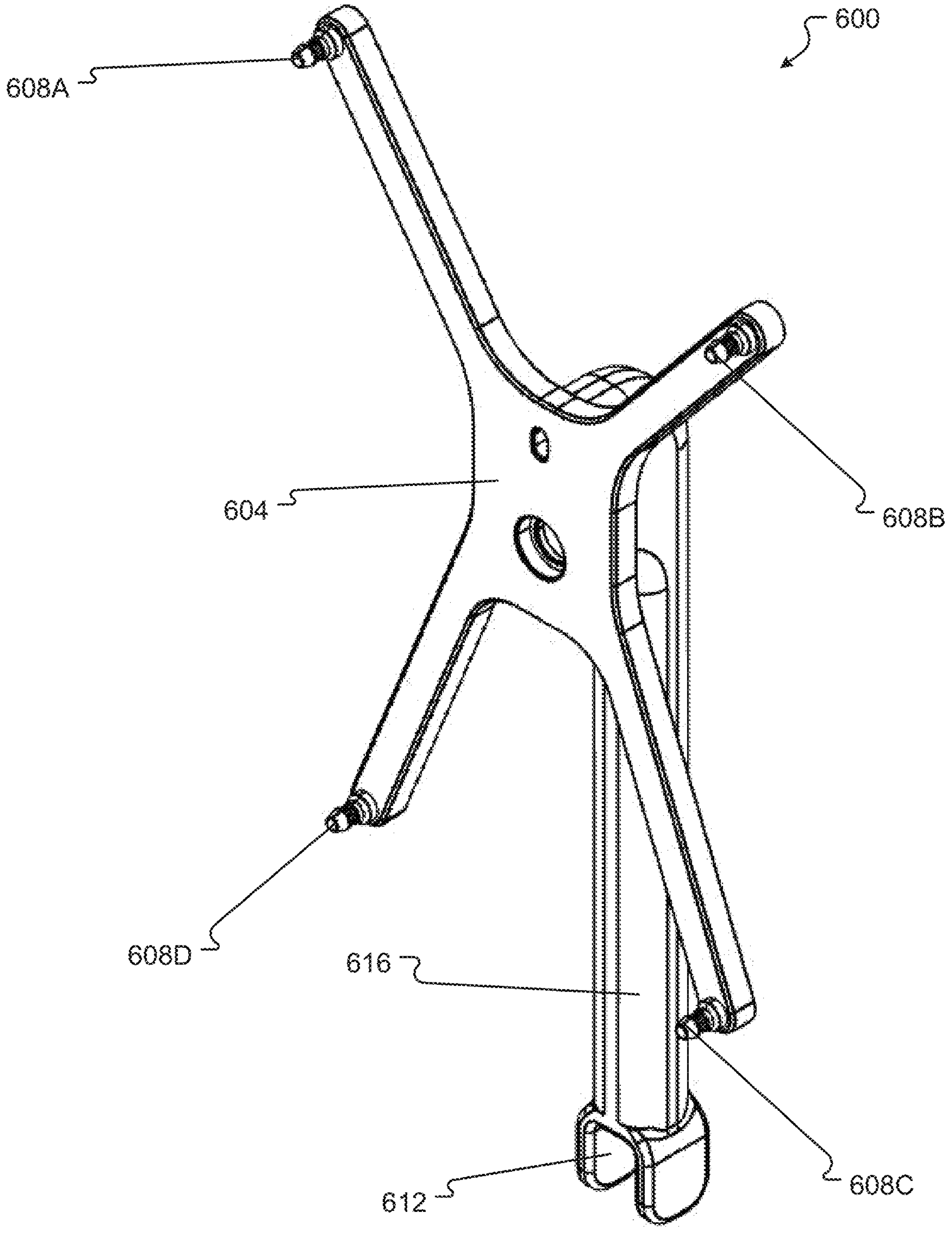
FIG. 6A show a perspective view of a navigation attachment in accordance with embodiments of the present disclosure.
Figure 6B:
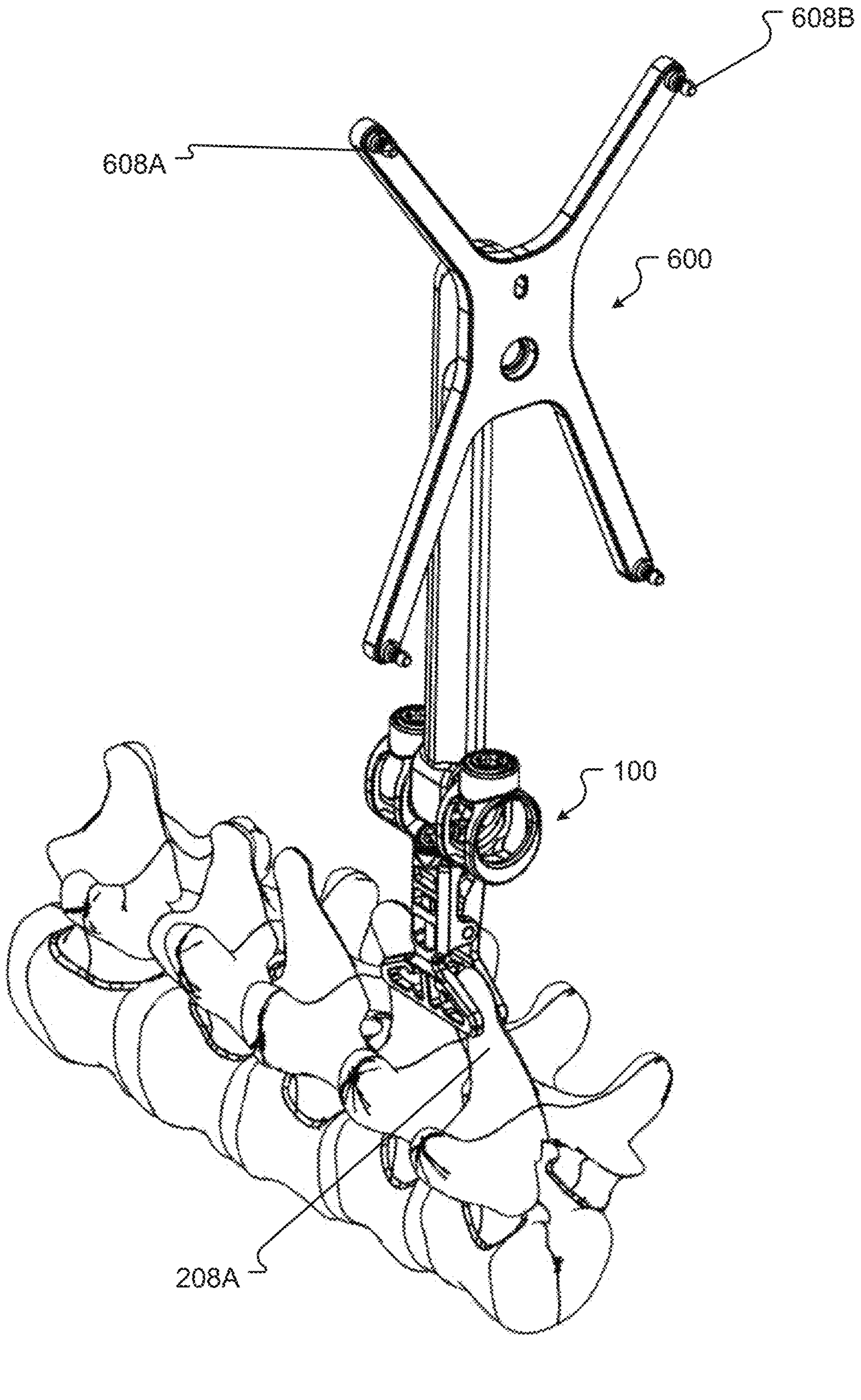
FIG. 6B shows a perspective view of the navigation attachment coupled with the bone mount device in accordance with embodiments of the present disclosure.

In some embodiments, a navigation attachment 600 may be used to determine the pose of the bone mount device 100. The navigation attachment 600 may include a body 604 to which one or more tracking markers 608A-608D may be attached. In some embodiments, the tracking markers 608A-608D may be similar to or the same as the tracking markers 508A-508E. The body 604 may be attached to a post 616 of a known length. The post 616 may support the body 604 and position the body 604 above the bone mount device 100 when the navigation attachment 600 is coupled with the bone mount device 100, such that one or more images of the navigation attachment 600 can be captured by an imaging device. The navigation attachment 600 may also include an attachment mechanism 612 to enable the navigation attachment 600 to be attached to the bone mount device 100. The attachment mechanism 612 may include, for example, one or more slots that can allow the navigation attachment 600 to be placed onto the bone mount device 100, as shown in FIG. 6B. One or more images of the navigation attachment 600 may be captured by an imaging device, and a pose of the navigation attachment 600 may be determined. Based on the pose of the navigation attachment 600, the relationship between the attachment mechanism 612 and the bone mount device 100, and a part number of the bone mount device 100, the navigation system may determine a position of the bone mount device 100. Similarly, the pose of the tracking markers 608A-608D may provide information necessary for the navigation system to determine the angle of the bone mount device 100. For instance, if the navigation attachment 600 is attached to the bone mount device 100 as shown in FIG. 6B, and a first tracking marker 608A has a height coordinate that is greater than a height coordinate of a second tracking marker 608B, the navigation system may determine the bone mount device 100 is tilted at a first angle.

Figure 7:
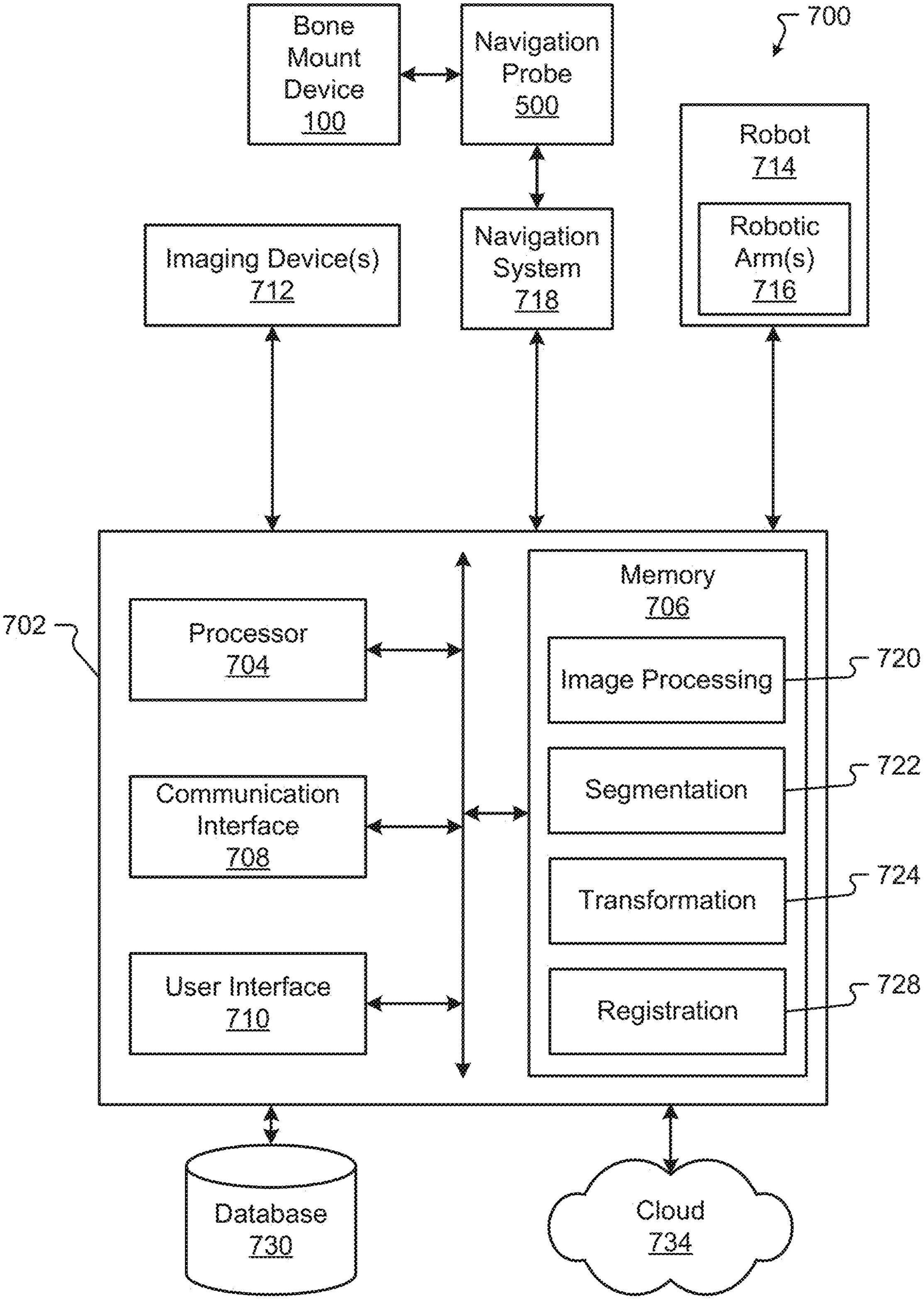
FIG. 7 shows a block diagram of a system in accordance with embodiments of the present disclosure.

Turning to FIG. 7, a block diagram of a system 700 according to at least one embodiment of the present disclosure is shown. The system 700 may be used to pose, and/or otherwise manipulate a surgical mount system, a surgical arm, and/or surgical tools attached thereto and/or carry out one or more other aspects of one or more of the methods disclosed herein. The system 700 comprises a computing device 702, one or more imaging devices 712, a robot 714, a navigation system 718, a database 730, and/or a cloud or other network 734. Systems according to other embodiments of the present disclosure may comprise more or fewer components than the system 700. For example, the system 700 may not include the imaging device 712, the robot 714, the navigation system 718, one or more components of the computing device 702, the database 730, and/or the cloud 734.

The computing device 702 comprises a processor 704, a memory 706, a communication interface 708, and a user interface 710. Computing devices according to other embodiments of the present disclosure may comprise more or fewer components than the computing device 702.

The processor 704 of the computing device 702 may be any processor described herein or any similar processor. The processor 704 may be configured to execute instructions stored in the memory 106, which instructions may cause the processor 704 to carry out one or more computing steps utilizing or based on data received from the imaging device 712, the robot 714, the navigation system 718, the database 730, and/or the cloud 734.

The memory 706 may be or comprise RAM, DRAM, SDRAM, other solid-state memory, any memory described herein, or any other tangible, non-transitory memory for storing computer-readable data and/or instructions. The memory 706 may store information or data useful for completing, for example, any step of the method 800 described herein, or of any other methods. The memory 706 may store, for example, instructions and/or machine learning models that support one or more functions of the robot 714. For instance, the memory 706 may store content (e.g., instructions and/or machine learning models) that, when executed by the processor 704, enable image processing 720, segmentation 722, transformation 724, and/or registration 728. Such content, if provided as in instruction, may, in some embodiments, be organized into one or more applications, modules, packages, layers, or engines. Alternatively or additionally, the memory 706 may store other types of content or data (e.g., machine learning models, artificial neural networks, deep neural networks, etc.) that can be processed by the processor 704 to carry out the various method and features described herein. Thus, although various contents of memory 106 may be described as instructions, it should be appreciated that functionality described herein can be achieved through use of instructions, algorithms, and/or machine learning models. The data, algorithms, and/or instructions may cause the processor 704 to manipulate data stored in the memory 706 and/or received from or via the imaging device 712, the robot 714, the database 730, and/or the cloud 734.

The computing device 702 may also comprise a communication interface 708. The communication interface 708 may be used for receiving image data or other information from an external source (such as the imaging device 712, the robot 714, the navigation system 718, the database 730, the cloud 734, and/or any other system or component not part of the system 700), and/or for transmitting instructions, images, or other information to an external system or device (e.g., another computing device 702, the imaging device 712, the robot 714, the navigation system 718, the database 730, the cloud 734, and/or any other system or component not part of the system 700). The communication interface 708 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 708 may be useful for enabling the computing device 702 to communicate with one or more other processors 704 or computing devices 702, whether to reduce the time needed to accomplish a computing-intensive task or for any other reason.

The computing device 702 may also comprise one or more user interfaces 710. The user interface 710 may be or comprise a keyboard, mouse, trackball, monitor, television, screen, touchscreen, and/or any other device for receiving information from a user and/or for providing information to a user. The user interface 710 may be used, for example, to receive a user selection or other user input regarding any step of any method described herein. Notwithstanding the foregoing, any required input for any step of any method described herein may be generated automatically by the system 700 (e.g., by the processor 704 or another component of the system 700) or received by the system 700 from a source external to the system 700. In some embodiments, the user interface 710 may be useful to allow a surgeon or other user to modify instructions to be executed by the processor 704 according to one or more embodiments of the present disclosure, and/or to modify or adjust a setting of other information displayed on the user interface 710 or corresponding thereto.

Although the user interface 710 is shown as part of the computing device 702, in some embodiments, the computing device 702 may utilize a user interface 710 that is housed separately from one or more remaining components of the computing device 702. In some embodiments, the user interface 710 may be located proximate one or more other components of the computing device 702, while in other embodiments, the user interface 710 may be located remotely from one or more other components of the computing device 702.

The imaging device 712 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 712, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 712 may be used to obtain first image data (e.g., a first image) at a first time, and a second imaging device 712 may be used to obtain second image data (e.g., a second image) at a second time after the first time. The imaging device 712 may be capable of taking a 2D image or a 3D image to yield the image data. The imaging device 712 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MM) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 712 suitable for obtaining images of an anatomical feature of a patient. The imaging device 712 may be contained entirely within a single housing, or may comprise a transmitter/emitter and a receiver/detector that are in separate housings or are otherwise physically separated.

In some embodiments, the imaging device 712 may comprise more than one imaging device 712. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 712 may be operable to generate a stream of image data. For example, the imaging device 712 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 714 may be any surgical robot or surgical robotic system. The robot 714 may be or comprise, for example, the Mazor X™ Stealth Edition robotic guidance system. The robot 714 may be configured to position the imaging device 712 at one or more precise position(s) and orientation(s), and/or to return the imaging device 712 to the same position(s) and orientation(s) at a later point in time. The robot 714 may additionally or alternatively be configured to manipulate a surgical tool (whether based on guidance from the navigation system 718 or not) to accomplish or to assist with a surgical task. In some embodiments, the robot 714 may be configured to hold and/or manipulate an anatomical element during or in connection with a surgical procedure. The robot 714 may comprise one or more robotic arms 716. In some embodiments, the robotic arm 716 may comprise a first robotic arm and a second robotic arm, though the robot 714 may comprise more than two robotic arms. In some embodiments, one or more of the robotic arms 716 may be used to hold and/or maneuver the imaging device 712. In embodiments where the imaging device 712 comprises two or more physically separate components (e.g., a transmitter and receiver), one robotic arm 716 may hold one such component, and another robotic arm 716 may hold another such component. Each robotic arm 716 may be positionable independently of the other robotic arm. The robotic arms 716 may be controlled in a single, shared coordinate space, or in separate coordinate spaces.

The robot 714, together with the robotic arm 716, may have, for example, one, two, three, four, five, six, seven, or more degrees of freedom. Further, the robotic arm 716 may be positioned or positionable in any pose, plane, and/or focal point. The pose includes a position and an orientation. As a result, an imaging device 712, surgical tool, or other object held by the robot 714 (or, more specifically, by the robotic arm 716) may be precisely positionable in one or more needed and specific positions and orientations.

The robotic arm(s) 716 may comprise one or more sensors that enable the processor 704 (or a processor of the robot 714) to determine a precise pose in space of the robotic arm (as well as any object or element held by or secured to the robotic arm).

In some embodiments, reference markers (e.g., navigation markers or tracking markers) may be placed on the robot 714 (including, e.g., on the robotic arm 716), the imaging device 712, or any other object in the surgical space. The reference markers may be tracked by the navigation system 718, and the results of the tracking may be used by the robot 714 and/or by an operator of the system 700 or any component thereof. In some embodiments, the navigation system 718 can be used to track other components of the system (e.g., imaging device 712) and the system can operate without the use of the robot 714 (e.g., with the surgeon manually manipulating the imaging device 712 and/or one or more surgical tools, based on information and/or instructions generated by the navigation system 718, for example).

The navigation system 718 may provide navigation for a surgeon and/or a surgical robot during an operation. The navigation system 718 may be any now-known or future-developed navigation system, including, for example, the Medtronic StealthStation™ S8 surgical navigation system or any successor thereof. The navigation system 718 may include one or more cameras or other sensor(s) for tracking one or more reference markers, navigated trackers, or other objects within the operating room or other room in which some or all of the system 700 is located. The one or more cameras may be optical cameras, infrared cameras, or other cameras. In some embodiments, the navigation system 718 may comprise one or more electromagnetic sensors. In various embodiments, the navigation system 718 may be used to track a position and orientation (e.g., a pose) of the imaging device 712, the robot 714 and/or robotic arm 716, and/or one or more surgical tools (or, more particularly, to track a pose of a navigated tracker attached, directly or indirectly, in fixed relation to the one or more of the foregoing). The navigation system 718 may include a display for displaying one or more images from an external source (e.g., the computing device 702, imaging device 712, or other source) or for displaying an image and/or video stream from the one or more cameras or other sensors of the navigation system 718. In some embodiments, the system 700 can operate without the use of the navigation system 718. The navigation system 718 may be configured to provide guidance to a surgeon or other user of the system 700 or a component thereof, to the robot 714, or to any other element of the system 700 regarding, for example, a pose of one or more anatomical elements, whether or not a tool is in the proper trajectory, and/or how to move a tool into the proper trajectory to carry out a surgical task according to a preoperative or other surgical plan. In some embodiments, the navigation system 718 may make use of the processor 704 or any other processor or processing unit to perform one or more determinations, calculations, or mathematical operations, or to access content stored in the memory 706.

The database 730 may store information that correlates one coordinate system to another (e.g., one or more robotic coordinate systems to a patient coordinate system and/or to a navigation coordinate system). The database 730 may additionally or alternatively store, for example, one or more surgical plans (including, for example, pose information about a target and/or image information about a patient's anatomy at and/or proximate the surgical site, for use by the robot 714, the navigation system 718, and/or a user of the computing device 702 or of the system 700); one or more images useful in connection with a surgery to be completed by or with the assistance of one or more other components of the system 700; and/or any other useful information. The database 730 may be configured to provide any such information to the computing device 702 or to any other device of the system 700 or external to the system 700, whether directly or via the cloud 734. In some embodiments, the database 730 may be or comprise part of a hospital image storage system, such as a picture archiving and communication system (PACS), a health information system (HIS), and/or another system for collecting, storing, managing, and/or transmitting electronic medical records including image data.

The cloud 734 may be or represent the Internet or any other wide area network. The computing device 702 may be connected to the cloud 734 via the communication interface 708, using a wired connection, a wireless connection, or both. In some embodiments, the computing device 702 may communicate with the database 730 and/or an external device (e.g., a computing device) via the cloud 734.

The system 700 or similar systems may be used, for example, to carry out one or more aspects of the method 800 described herein. The system 700 or similar systems may also be used for other purposes.

FIG. 8 depicts a method 800 that may be used, for example, to determine a pose of a bone mount device.

One or more steps of the method 800 may be carried out or otherwise performed, for example, by at least one processor. The at least one processor may be the same as or similar to the processor(s) 704 of the computing device 702 described above. The at least one processor may be part of a robot (such as a robot 714) or part of a navigation system (such as a navigation system 718). A processor other than any processor described herein may also be used to execute one or more steps of the method 800. The at least one processor may perform the method 800 by executing elements stored in a memory such as the memory 706. The elements stored in the memory and executed by the processor may cause the processor to execute one or more steps of a function as shown in method 800. One or more portions of a method 800 may be performed by the processor executing any of the contents of memory, such as an image processing 720, a segmentation 722, a transformation 724, and/or a registration 728.

The method 800 comprises receiving a plurality of images depicting a navigation probe contacting one or more divots on a medical instrument (step 804). The navigation probe may be similar to or the same as the navigation probe 500 or the navigation attachment 600, while the medical instrument may be or comprise a medical device, surgical device, or the like and may be similar to or the same as the bone mount device 100. The one or more divots may be similar to or the same as the plurality of divots 108. The plurality of images may be or comprise image data or information captured by one or more imaging devices such as the imaging devices 712 that depict the navigation probe 500 or the navigation attachment 600 relative to the plurality of divots 108.

Each separate image of the plurality of images may depict the navigation probe 500 (and the tracking markers 508A-508E thereof) contacting a separate divot. For example, a first image (or image data or image information) may depict the navigation probe 500 positioned such that the navigation probe tip 304 of the navigation probe 500 is disposed, coupled with, slotted into, or otherwise touching the first divot 108A. Similarly, a second image may depict the navigation probe 500 touching the second divot 108B, and a third image may depict the navigation probe 500 touching the third divot 108C. In some embodiments, there may be one or more images depicting different views of the navigation probe 500 contacting each of the first divot 108A, the second divot 108B, and the third divot 108C.

In other embodiments, the plurality of divots 108 may each be reflective, radiopaque, or may otherwise be detectable in the captured images. In such embodiments, a navigation system 718 using a processor 704 may be able to further process the images (e.g., using image processing 720) to label or otherwise identify the plurality of divots 108 in the images.

In one embodiment, the plurality of images may be captured by the imaging devices 712 based on the positioning of the navigation probe 500 by a user. For example, the user (e.g., a physician) may select an option on the user interface 710 to define the medical instrument. The user may then be prompted (e.g., based on a message displayed on the user interface 710) to place the navigation probe 500 such that the navigation probe tip 304 contacts the first divot 108A. Once the user has positioned the navigation probe tip 304 in the first divot 108A, a first image may be captured. The user may then be further prompted to repeat the placement of the navigation probe tip 304 in the second divot 108B, the third divot 108C, and one or more other divots present on the medical instrument. Additionally images of each placement may also be captured.

The method 800 also comprises registering, based on the plurality of images, each divot of the plurality of divots (step 808). Based on the pose of the navigation probe 500 in each image of the plurality of images and, more specifically, the pose of the tracking markers 508A-508E relative to the navigation probe tip 304, the navigation system 718 may determine a location of each divot in space. For example, the navigation probe tip 304 may be a known distance from each of the tracking markers 508A-508E. The navigation system 718 may use image processing 720 to identify each tracking marker of the tracking markers 508A-508E in a first image and determine the position of each tracking marker in 3D space (e.g., based on the position of the tracking markers 508A-508E relative to a known location in 3D space). Then, based on information about the position of the tracking markers 508A-508E relative to the navigation probe tip 304, the navigation system 718 may determine a position of the first divot 108A in 3D space. The image processing and determining the position of the divot may then be repeated for the second divot 108B, the third divot 108C, as well as for one or more other divots on the medical instrument.

The navigation system 718 may use registration 728 to register each divot to a coordinate system. The coordinate system may be a common coordinate system shared by one or more surgical tools or instruments (e.g., a coordinate system used by the navigation system 718 to navigate the robotic arm 716), to an anatomical element coordinate system (e.g., a coordinate system used by the navigation system 718 to maneuver a surgical implant such as a pedicle screw into a vertebra), or to any other coordinate system. Each divot of the plurality of divots 108 may be registered into one or more coordinate systems, such that the navigation system 718 knows coordinates associated with the divot in the one or more coordinate systems.

The method 800 also comprises receiving information about the medical instrument (step 812). The information about the medical instrument may be received from one or more sources, such as from the user (e.g., through the user interface 710), from the database 730, from another computing device 702, or from any other source. The information about the medical instrument may include information about the dimensions of the medical instrument (e.g., length, width, height, etc.), center of mass, the positions of each divot on the medical instrument, and the like. In one embodiment, the information about the medical instrument may be or comprise a part number or other identification number. Based on the part number, the navigation system 718 may be able to access further information about the medical instrument (e.g., accessing a specification sheet stored in the database 730). For example, a first part number may be provided to the navigation system 718 by the user. The navigation system 718 (using a processor 704) may access the database 730 to find information about the medical instrument that matches the first part number, and may retrieve information about an orientation or configuration of the plurality of divots 108. In other embodiments, the surgical instrument may have a unique pattern to the divots. In other words, the orientation of the divots may be unique to the surgical instrument. In such embodiments, the navigation system 718 may determine, based on the position of each divot, the relative distances between each divot, and may use the determination to identify a 3D model of the medical instrument, as discussed in step 816 below. For example, one or more 3D models (e.g., Computer Aided Design (CAD) models or designs) associated with one or more surgical instruments may be stored in the database 730, with each surgical instrument including a unique divot pattern. Based on the unique pattern (e.g., unique distances between the divots, unique geometric patterns of the divots, etc.), the navigation system 718 may identify the corresponding 3D model.

The method 800 also comprises determining, based on the received information about the medical instrument and the registration of each divot, a position of the medical instrument (step 816). The navigation system 718 may use the 3D model corresponding to the medical instrument, as well as the registered divot points, to define a position of the medical instrument in 3D space. For example, the navigation system 718 may use the coordinates associated with the divots, and the 3D model that includes the divots, and use one or more transformations 724 to determine a set of points that represent the position of the medical instrument in a coordinate system. In some embodiments, the navigation system 718 may render the coordinates to a display (e.g., the user interface 710) along with a rendering of the anatomical element to which the medical instrument is attached, and may highlight a perimeter of the volume occupied by the medical instrument so that the user can view where the medical instrument is relative to the anatomical element and/or relative to a planned trajectory of a medical implant, such as a surgical screw.

The method 800 also comprises determining, based on the plurality of images, a position of a moveable component divot relative to at least one divot of the plurality of divots (step 820). The plurality of images may include one or more images (or image data or other information) depicting the navigation probe 500 positioned such that the navigation probe tip 304 is disposed on an adjustor divot, which may be similar to or the same as the fourth divot 112. For example, the medical instrument may be similar to or the same as the bone mount device 100, and may include a set screw 120 or other attachment mechanism that enables the bone mount device 100 to connect to an anatomical element. While the divots registered in the step 808 may be used to determine a position of the bone mount device 100, the position of fourth divot 112 may be used to determine an angle of the clamp 110 or of another component of the bone mount device 100 relative to the anatomical element.

Based on the image, the navigation system 718 may identify the tracking markers 508A-508E of the navigation probe 500 and register the fourth divot 112 to a common coordinate system, similar to the step 808 above. Based on the registration, the navigation system 718 may then know the position of the fourth divot 112. Alternatively, the navigation system 718 may compare pose of the tracking markers 508A-508E when the navigation probe tip 304 contacts the fourth divot 112 with the pose of the tracking markers 508A-508E when the navigation probe tip 304 contacts any of the other divots of the plurality of divots 108 to determine a position of the fourth divot 112 relative to one or more divots of the plurality of divots 108.

The method 800 also comprises determining, based on the position of the moveable component divot and the information about the medical instrument, an angle of the medical instrument (step 824). The angle of the medical instrument may correspond to a calculated angle of the clamp 110. The difference between the position of the fourth divot 112 and any one or more divots of the plurality of divots 108 may reflect the angle of the clamp. For example, when the fourth divot 112 and the third divot 108C are separated by a first distance 404 in a first direction, the clamp may be at a first angle 408, while the clamp 110 may be at a second angle 416 when the fourth divot 112 and the third divot 108C are separated by a second distance 412 in the first direction. While examples have been discussed with respect to the distance between the fourth divot 112 and the third divot 108C, the distance between the fourth divot 112 and any one or more of the divots of the plurality of divots 108 may be used to determine the angle of the clamp 110.

In some embodiments, the navigation system 718 may use one or more predetermined tables, charts, or values to determine the clamp angle, or may perform one or more mathematical calculations to determine the clamp angle. For example, the bone mount device 100 may have predetermined angles based on the distance between the fourth divot 112 and any one or more divots of the plurality of divots 108, as determined and published by, for example, a manufacturer.

The method 800 also comprises registering the medical instrument to an anatomical element (step 828). By determining the position and angle of the medical instrument, the navigation system 718 may know the 3D space (e.g., volume) occupied by the medical instrument. The navigation system 718 may then use registration 728 to register one or more points on the medical instrument to the anatomical element (e.g., a vertebra). In some embodiments, the navigation system 718 may register an outline (e.g., the perimeter or boarder) of the medical instrument to the anatomical element, which may save computation time while also ensuring the medical instrument and the anatomical element are represented in a common coordinate system. In some embodiments, the medical instrument may be registered into additional or alternative coordinate system, such as a common coordinate system shared by other medical instruments or devices, a coordinate system associated with a robotic arm, combinations thereof, and the like.

The method 800 also comprises updating, based on the position and angle of the medical instrument, a surgical plan (step 832). The surgical plan may specify that a medical implant, like a pedicle screw, is to be maneuvered (e.g., using a robotic arm) along a first trajectory to be inserted into an anatomical element such as a vertebra. The navigation system 718 may determine whether, based on the position and angle (e.g., pose) of the medical instrument, the first trajectory would result in a collision between the pedicle screw and the medical instrument, or if any other collision could occur based on the pose of the medical instrument. In some embodiments, the navigation system 718 may compare whether the path taken by the pedicle screw would cross through or occupy coordinates associated with the medical instrument. If the pedicle screw would cross through the coordinates associated with the medical instrument, the navigation system 718 may determine that a collision would occur, and may determine a new trajectory for the pedicle screw. The navigation system 718 may determine the new trajectory of the pedicle screw based on the coordinates of the medical instrument, such that the new trajectory does not cross through or occupy coordinates associated with the medical instrument. In some embodiments, the surgeon or other member of the surgical staff may determine that the surgical plan should be updated. For example, the physician may view a rendering of the proposed trajectory on a screen or other monitor, and may determine that the trajectory of the screw should be updated. The physician may then provide one or more inputs (e.g., by manipulating a touchscreen on the display) to cause the surgical plan to be updated. Alternatively, the physician may keep the original trajectory, but may adjust the pose of the clamp, such that the clamp is no longer positioned along the original trajectory of the screw.

In some embodiments, the navigation system 718 may use a threshold tolerance for determining whether to adjust the trajectory. For example, the navigation system 718 may define a minimum distance between the pedicle screw and the medical instrument that would need to be maintained at all times while the pedicle screw follows the planned trajectory. If the pedicle screw is ever within a distance of the medical instrument that is below the minimum distance, the navigation system 718 may indicate that the trajectory needs to be updated. Similarly, the navigation system 718 may take into account the minimum distance when determining the new trajectory, such as by ensuring that the new trajectory does not pass the pedicle screw within a distance of the medical instrument that is below the minimum distance threshold.

The present disclosure encompasses embodiments of the method 800 that comprise more or fewer steps than those described above, and/or one or more steps that are different than the steps described above.

As noted above, the present disclosure encompasses methods with fewer than all of the steps identified in FIG. 8 (and the corresponding description of the method 800), as well as methods that include additional steps beyond those identified in FIG. 8 (and the corresponding description of the method 800). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim.

Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method, comprising:
- receiving a plurality of images, the plurality of images depicting a navigation probe contacting each of at least a first divot, a second divot, a third divot, and a fourth divot on a medical instrument, wherein the first divot, the second divot, and the third divot are disposed on an upper body of the medical instrument, and wherein the fourth divot is disposed on a screw of the medical instrument;
- receiving information about the medical instrument; and
- determining, based on the plurality of images and the information, a pose of the medical instrument.

2. The method of claim 1, further comprising:
- updating, based on the pose of the medical instrument, a surgical plan.

3. The method of claim 2, wherein updating the surgical plan further comprises:
- registering the medical instrument to an anatomical element; and
- determining, based on the registering, a new trajectory for a surgical implant.

4. The method of claim 3, wherein the surgical implant includes a pedicle screw.

5. The method of claim 1, wherein the medical instrument comprises a bone mounting device, wherein the information about the medical instrument comprises information about a pre-configured orientation of the first divot, the second divot, the third divot, and the fourth divot, and wherein the navigation probe contacts each divot of the first divot, the second divot, the third divot, and the fourth divot in a sequence.

6. The method of claim 5, wherein determining the pose of the medical instrument further comprises:
- determining a pose of a plurality of tracking markers on the navigation probe when the navigation probe contacts each of the first divot, the second divot, the third divot, and the fourth divot; and
- determining, based on the pre-configured orientation and the determined pose of the plurality of tracking markers, a position of the medical instrument.

7. A system, comprising:
- a surgical device comprising:
  - an upper body with a first divot, a second divot, and a third divot;
  - a clamp connected to the upper body and configured to attach the surgical device to an anatomical element; and
  - a screw that secures the clamp to the anatomical element, the screw comprising a fourth divot;
- a processor; and
- a memory storing data thereon that, when processed by the processor, cause the processor to:
  - receive a plurality of images depicting a navigation probe contacting each of the first divot, the second divot, the third divot, and the fourth divot;
  - receive information about the surgical device; and
  - determine, based on the plurality of images and the information about the surgical device, a pose of the surgical device.

8. The system of claim 7, wherein the data further cause the processor to:
- receive at least one image depicting the navigation probe contacting the fourth divot;
- determine, based on the at least one image and the information about the surgical device, a position of the fourth divot relative to at least one of the first divot, the second divot, and the third divot; and
- determine, based on the position, an angle of the surgical device relative to the anatomical element.

9. The system of claim 7, wherein each of the first divot, the second divot, the third divot, and the fourth divot includes a first geometric shape, and wherein the first geometric shape is one of a circle, a triangle, a square, a rectangle, a pentagon, a hexagon, a heptagon, an octagon, a nonagon, a decagon, an ellipse, a trapezoid, a parallelogram, a rhombus, a cross or a plus, a pentagram, a hexagram, an octagram, or a crescent.

10. The system of claim 7, wherein the fourth divot is disposed in a hollow interior of the screw.

11. The system of claim 7, wherein the data further cause the processor to:
- update, based on the pose of the surgical device, a surgical plan.

12. The system of claim 11, wherein updating the surgical plan further comprises:
- registering the surgical device to an anatomical element; and
- updating, based on the registering, a trajectory of a surgical implant.

13. The system of claim 7, wherein the clamp comprises a first jaw and a second jaw.

14. The system of claim 13, wherein the screw is threaded through the upper body to contact at least one of the first jaw and the second jaw.

15. An apparatus, comprising:
- an imaging device;
- a bone mount device configured to attach to an anatomical element, the bone mount device comprising:
  - an upper body with a first divot, a second divot, and a third divot;
  - a clamp connected to the upper body; and
  - a screw component that attaches the clamp to the anatomical element, the screw component comprising a fourth divot;
- a processor; and
- a memory storing data thereon that, when processed by the processor, cause the processor to:
  - receive a plurality of images from the imaging device depicting a plurality of navigation markers disposed on a navigation probe that contacts each of the first divot, the second divot, the third divot, and the fourth divot;

receive information about an orientation of the first divot, the second divot, the third divot, and the fourth divot; and determine, based on the plurality of images and the information about the orientation of the first divot, the second divot, the third divot, and the fourth divot, a pose of the bone mount device.

16. The apparatus of claim 15, wherein the navigation probe is perpendicular to a surface of the bone mount device when contacting at least one of the first divot, the second divot, the third divot, er and the fourth divot.

17. The apparatus of claim 15, wherein the data further cause the processor to:

update, based on the pose of the bone mount device, a surgical plan.

18. The apparatus of claim 17, wherein updating the surgical plan further comprises:

registering the bone mount device to the anatomical element; and updating, based on the registering, a trajectory for a surgical implant.

19. The apparatus of claim 15, wherein the bone mount device is attached to a spinous process of a vertebra, and wherein the apparatus further comprises:

a connector coupled to the bone mount device at a first end and coupled to a robotic arm at a second end.

20. The apparatus of claim 19, wherein the first end of the connector is inserted into a first port of the bone mount device.

* * * * *